US012447001B2

(12) United States Patent
Nigon

(10) Patent No.: US 12,447,001 B2
(45) Date of Patent: Oct. 21, 2025

(54) UMBRELLA TYPE FILTER WITH ANTI-TRANSFIXION PROTECTION

(71) Applicant: A.L.N., Ghisonaccia (FR)

(72) Inventor: Alain Nigon, Bormes les Mimosas (FR)

(73) Assignee: A. L. N., Bormes les Mimosas (FR)

( * ) Notice: Subject to any disclaimer, the term of this patent is extended or adjusted under 35 U.S.C. 154(b) by 301 days.

(21) Appl. No.: 17/043,078

(22) PCT Filed: Apr. 18, 2019

(86) PCT No.: PCT/FR2019/050934
§ 371 (c)(1),
(2) Date: Sep. 29, 2020

(87) PCT Pub. No.: WO2019/202274
PCT Pub. Date: Oct. 24, 2019

(65) Prior Publication Data

US 2021/0015596 A1 Jan. 21, 2021

(30) Foreign Application Priority Data

Apr. 18, 2018 (FR) ....................................... 1853412

(51) Int. Cl.
*A61F 2/01* (2006.01)

(52) U.S. Cl.
CPC .......... *A61F 2/0103* (2020.05); *A61F 2/0105* (2020.05); *A61F 2220/0016* (2013.01); (Continued)

(58) Field of Classification Search
CPC ........ A61B 17/12022; A61B 17/12109; A61B 17/12122; A61F 2/0105; A61F 2002/016; (Continued)

(56) References Cited

U.S. PATENT DOCUMENTS 4,494,531 A * 1/1985 Gianturco ................. A61F 2/01 606/200
4,781,177 A * 11/1988 Lebigot ................. A61F 2/0105 606/1
(Continued)

FOREIGN PATENT DOCUMENTS

| | | | |
|---|---|---|---|
| EP | 2997933 | A1 | 3/2016 |
| JP | 2016-509909 | A | 4/2016 |
| WO | 2011/055079 | A1 | 5/2011 |

OTHER PUBLICATIONS

Machine translation of Nigon (WO 2011/055079) (Year: 2011).*
(Continued)

*Primary Examiner* — Katherine Shi
(74) *Attorney, Agent, or Firm* — Morgan, Lewis & Bockius LLP

(57) ABSTRACT

The present invention concerns a filter (1) for a blood vessel, and in particular a vena cava filter, comprising at least two anchoring branches (11) for anchoring the filter in the wall of the blood vessel, the anchoring branches having a fixed end (111) and a free end (112), the fixed ends of the anchoring branches being fixed to one another and the free ends being terminated with a hook (113) oriented toward the outside, characterised in that each of the anchoring branches comprises an anti-transfixion protection (114).

17 Claims, 2 Drawing Sheets

(52) U.S. Cl.
CPC ................. *A61F 2230/0067* (2013.01); *A61F 2230/0093* (2013.01)

(58) Field of Classification Search
CPC .............................. A61F 2/0103; A61F 2/011; A61F 2220/0016; A61F 2250/0036; A61F 2/01; A61F 2/848; A61F 2002/8483; A61F 2230/0093
See application file for complete search history.

(56) References Cited

U.S. PATENT DOCUMENTS

2006/0015137 A1 1/2006 WasDyke et al.
2008/0033534 A1 2/2008 Cook et al.
2010/0049238 A1 2/2010 Simpson
2010/0121373 A1* 5/2010 Tekulve ................ A61F 2/0105 606/200
2010/0222772 A1* 9/2010 Kleshinski ............ A61F 2/0105 606/1
2011/0137335 A1* 6/2011 Hallisey .................. A61F 2/012 606/200
2013/0138137 A1* 5/2013 Molgaard-Nielsen ....................... A61F 2/0105 606/200
2016/0038270 A1 2/2016 Horan et al.
2016/0081785 A1* 3/2016 Dela ..................... A61F 2/0105 606/200

OTHER PUBLICATIONS

International Search Report issued in corresponding International Patent Application No. PCT/FR2019/050934 dated Jul. 5, 2019.
Office Action issued in related European Patent Application No. 19724556.6 dated Jan. 31, 2022.
Office Action issued in related Japanese Patent Application No. 2020-557895 dated Mar. 15, 2022.

* cited by examiner

UMBRELLA TYPE FILTER WITH ANTI-TRANSFIXION PROTECTION

TECHNICAL FIELD

The present invention relates to the technical field of medical devices and more particularly filters for blood vessels and in particular vena cava filters.

PRIOR ART

In order to prevent the sometimes fatal consequences of migrating deep vein thromboses, filters can be placed inside the vena cava and in particular in the lower part thereof. This is because these thromboses generally form on the wall of the veins in the lower limbs before breaking off and rising towards the heart through the inferior vena cava. If the thromboses reach the lungs, they may obstruct the pulmonary arteries, leading to a pulmonary embolism, which may prove fatal.

Vena cava filters make it possible to stop the thrombosis before it reaches the lungs by creating an obstacle stopping the advance thereof.

One example of a vena cava filter is a vena cava filter of the umbrella type. This type of filter generally comprises branches, each including a fixed end and a free end. The fixed ends of the branches being fixed to one another, in particular by crimping to a base, generally cylindrical in shape with a rounded end. The branches, referred to as anchoring branches, therefore extend from the base while moving away from one another like the ribs of an umbrella. Thus the anchoring branches give the filter an outer envelope having the shape of a cone or an onion dome. In other words, this envelope is formed by the revolution about an axis of a straight line intersecting this axis or of a curved line arising at a point close to the axis and extending while moving away therefrom.

In order to be effective, these vena cava filters of the umbrella type must be anchored to the wall of the vena cava. For this purpose, the free ends terminate in a hook oriented towards the outside. These hooks will be anchored into the wall of the vena cava in order to fix the position of the filter.

Unfortunately, in some cases, the anchoring branches pierce the wall of the vena cava, causing damage to an adjacent organ, which may give rise to internal bleeding, which may have serious consequences for the patient. In particular, in a retrospective review, "*Retrospective Review of* 120 *Celect Inferior Vena Cava Filter Retrievals: Experience at a Single Institution*" in J Vasc Interv Radiol 2012; 23:1557-1563, Zhou D. Y. and his team were able to observe a transfixion rate of 86.1% in the 115 patients who came to have the filter removed and for whom a cavogram by anteroposterior projection was available and of 65.8% in the 38 patients who came to have the filter removed and for whom a tomodensitometry image was available, including 9 in whom the transfixion had reached an organ adjacent to the site where the filter was placed. The authors concluded that the filter used had a high transfixion rate correlated with the period during which the filter remained in the inferior vena cava, although these figures do not take into account the patients in whom the filter was installed and who did not come to have the filter removed.

Moreover, it is important for these umbrella type vena cava filters to be correctly aligned with respect to the local axis of the vena cava, that is to say the direction of the axis of revolution of the envelope of these umbrella type vena cava filters must not be too different from that of the local axis of the vena cava. If the filter tilt exceeds a certain degree, the efficacy of the filter may be reduced.

For example, in a study of the Günther Tulip filter: "*Analysis of Tilt of the Günther Tulip Filter*" J Vasc Interv Radiol 2008; 19:669-676, Sag A. A. and his team observed that 159 patients among the 175 who came to have the filter removed exhibited a tilt of the filter where the mean tilting degree is 7.1°±5.8.

PRESENTATION OF THE INVENTION

Thus, one of the aims of the present invention is to overcome at least one of the disadvantages of the filters of the prior art mentioned above.

For this aim, the present invention provides a blood vessel filter, and in particular a vena cava filter, comprising at least two anchoring branches for anchoring the filter in the wall of the blood vessel, the anchoring branches including a fixed end and a free end, the fixed ends of the anchoring branches being fixed to one another and the free ends terminating in a hook oriented outwards, characterised in that each of the anchoring branches comprises a anti-transfixion protection.

Thanks to the anti-transfixion protection, any piercing of the wall of the blood vessel in which the filter is placed is avoided.

Other optional and non-limitative features of the filter are presented below.

The anti-transfixion protection may be a loop, a zigzag or an undulation produced on the anchoring branch in proximity to the hook. The anti-transfixion protection may be a loop having an equivalent diameter of between 990 and 1210 μm.

At least two anchoring branches may have different lengths.

The filter may further comprise three short centring branches, each comprising a fixed end and a free end, the fixed end being fixed to the fixed ends of the anchoring branches, and the free end being non-traumatic. The three short centring branches may be shorter than the anchoring branches. The non-traumatic free end may have a hook oriented inwards. The short centring branches may have equal lengths or different lengths.

The filter may further comprise three long centring branches, each having a fixed end and a free end, the fixed end being fixed to the fixed ends of the anchoring branches. The three long centring branches may be longer than the anchoring branches.

The filter may also comprise a contact branch having a fixed end and a free end. The fixed end being fixed to the fixed ends of the anchoring branches and the free end comprising a stop. The stop may be a loop produced from the contact branch.

The free end of one of the long centring branches may comprise a stop. The stop may be a loop produced from the long centring branch.

The filter may be entirely produced from stainless steel, in particular INOX 316 LVM.

The present invention also provides a blood vessel filter, and in particular a vena cava filter, comprising at least two anchoring branches for anchoring the filter in the wall of the blood vessel, the anchoring branches comprising a fixed end and a free end, the fixed ends of the anchoring branches being fixed to one another and terminating in a hook oriented outwards; and three centring branches shorter than the anchoring branches, each comprising a fixed end and a free end, the fixed end being fixed to the fixed ends of the anchoring branches, and the free end being non-traumatic.

Thank to these centring branches shorter than the anchoring branches, the tilting of the filter with respect to the ideal position thereof can be limited.

DRAWINGS

Other objectives, features and advantages will become apparent from reading the following illustrative description with reference to the drawings given non-limitatively and by way of example, among which:

DESCRIPTION

Figure 1:
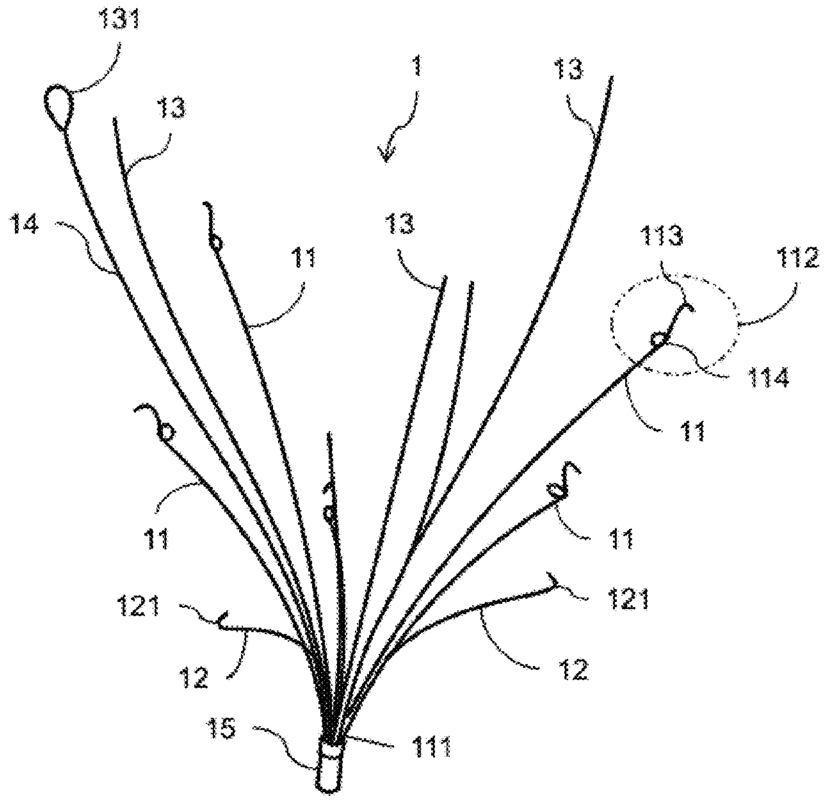
FIG. 1 is a three-quarter illustration of an example of a filter according to the invention.
Figure 2:
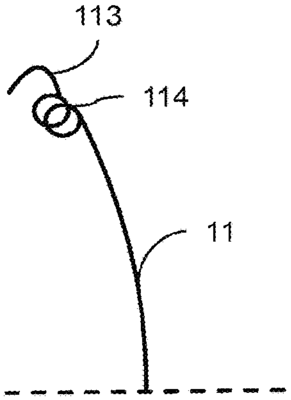
FIGS. 2 to 5 are magnified view of examples of anti-transfixion protection for the filter of FIG. 1.
Figure 3:
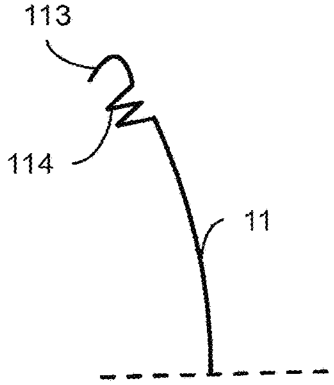
Figure 4:
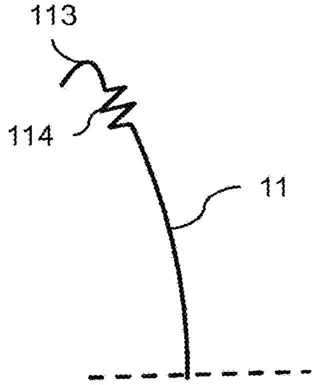

A blood vessel filter, in particular a vena cava filter, of the umbrella type according to the invention will be described below with reference to FIGS. 1 to 5.

Umbrella type filter 1 means filters comprising a plurality of branches 11, 12, 13, each branch having a fixed end and a free end. The fixed ends of the branches are fixed to one another by means of a member 15, the shape of which is generally a sphere, a spindle, a cylinder with a circular base, a nose cone, etc., the edges preferentially being rounded. Fixing is generally effected through crimping with or without laser welding. The branches 11, 12, 13 move progressively further apart from one another starting from the fixation point. Each of the branches 11, 12, 13 generally has a circular cross section. The branches 11, 12, 13 extend independently of one another and may form a straight line, a convex line, a concave line, a line having a inflection point with a first portion closer to the concave fixed end and a second portion closer to the convex free end, a line having an inflection point having a first portion closer to the convex free end and a second portion closer to the concave free end, etc. The concavity of the lines is considered from a point of view situated in the open space formed by the branches, that is to say inside the umbrella. The filter generally comprises a longitudinal axis. The longitudinal axis is the average of extension axes of the branches, the extension axis of a branch being an axis connecting its ends. Thus, preferably, if two points on the line formed by a branch are considered, the point closer to the fixed end is not further away from the longitudinal axis than the point closer to the free end. Preferably any branch can follow a line fitting within a plane, advantageously intersecting the longitudinal axis of the filter. The above description of the shape of the branches does not take into account the hooks and anti-transfixion protection, in particular those described below.

The filter 1 of the invention comprises at least two anchoring branches 11 (for example 2, 3, 4, 5, 6, 7, 8, 9, 10 anchoring branches) for anchoring the filter 1 in the wall of the blood vessel, the anchoring branches 11 comprising a fixed end 111 and a free end 112. The filter 1 of the invention preferably comprises at least 3, at least 4, at least 5, at least 6, at least 7, at least 8, at least 9 or at least 10 anchoring branches 11.

The fixed ends 111 of the anchoring branches are fixed to one another by means of the member 15 and the free ends 112 end in a hook 113 oriented towards the outside of the filter to allow anchoring of the filter 1 to the wall of the blood vessel. Advantageously, the hook 113 has an equivalent diameter of between 400 and 1100 μm, preferably between 750 and 950. In the present disclosure, the term "equivalent diameter" of a hook designates the diameter of the smallest circle in which the hook can be inscribed, from its end as far as the first local minimum radius of curvature, the latter being able to be zero.

Each of the anchoring branches 11 further comprises anti-transfixion protection 114. The anti-transfixion protection 114 may comprise a loop formed by the anchoring branch itself in proximity to the hook 113 (see FIGS. 1 and 2). In the present description, the term "loop" should be understood as designating the form adopted by a branch the line of which follows, in proximity to the hook, a curve closing on itself. At the point where the curve closes on itself, the two parts of the branch may be in contact or not, preferably they are in contact.

The loop advantageously has an equivalent diameter between 990 and 1210 μm, preferably between 1100 μm and 1150 μm. In the present disclosure, the term "equivalent diameter" of a loop designates the diameter of the smallest circle in which the projection of the loop onto a plane with the largest inner area can be inscribed. Preferably, the shape of the projection of the loop onto a plane with the largest inner area is a circle.

The loops of two different branches may be of different diameters. They may alternatively have the same diameter. Preferably, the loops of all the branches have the same diameter with a tolerance of ±10%. Still preferably, the loops of all the branches are circles.

The loops of two different branches may have different shapes. They may alternatively have the same shape.

The number of loops may be increased, for example at least 2, at least 3 or at least 4. When there is more than one loops, the loops may be disposed either adjacent to one another or one completely or partially overlapping the others. In this case, apart from the possibilities described above, all the loops of the same branch may have different diameters. They may alternatively have the same diameter. Preferably, the loops of all the branches have the same diameter with a tolerance of +10%. Still preferably, the loops of all the branches are circles. Furthermore, they may have different forms. They may alternatively have the same form.

Figure 5:
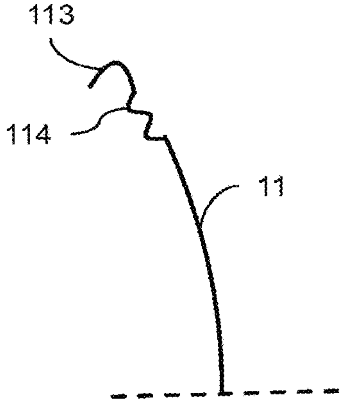

Other shapes of anti-transfixion protection are also possible, for example:

- the zigzag (sawtooth) form, in particular having 1, 2, 3 periods or more, and/or where the angle of the vertices is between 30° and 90°, for example 40°, 45°, 50°, 60°, 70°, 80°, and/or the peak-to-peak width is advantageously between 990 and 1210 μm, preferably between 1100 μm and 1150 μm (FIGS. 3 and 4); and
- an wavy form (undulation), in particular having 1, 2, 3 periods or more, and/or the peak-to-peak width is advantageously between 990 and 1210 μm, preferably between 1100 μm and 1150 μm, and/or a period length of between 1 and 5 mm (see FIG. 5). These shapes are disposed like the loop in proximity to the hook. The size of the anti-transfixion protections makes it notably possible to avoid endothelisation of the filter for a removal which is safe and less traumatic for the patient.

At least two anchoring branches 11 may have different lengths. This makes it possible to avoid the hooks thereof hooking on each other when the filter is deployed as described below. Preferably, the anchoring branches have different lengths from one another.

The line followed by each anchoring branch 11 may have one of the shapes described above. Preferably, the lines followed by the anchoring branches 11 are convex.

The filter may also comprise at least three short centring branches 12 (for example 3, 4, 5, 6 short centring branches). The line followed by each short centring branch 12 may have one of the shapes described above. Preferably, the lines followed by the short centring branches 12 are convex. The short centring branches 12 are preferably shorter than the anchoring branches 11. Preferably from 35% to 55%, still preferably 40% to 50%, again preferably approximately 45%, shorter than the shortest anchoring branch. The short centring branches 12 may be of different or equal lengths. Preferably, they are of equal lengths.

Each short centring branch 12 has a fixed end and a free end, the fixed end being fixed to the fixed ends of the anchoring branches in particular by the piece 15, and the free end being non-traumatic.

The non-traumatic character of the free end can be conferred by a short hook 121 oriented inwards, in particular when the line of the short centring branch 12 is convex. Thus the curve formed by the branch at the hook is oriented towards the wall of the blood vessel when the filter is in place, avoiding injuring it. Advantageously, the hook 121 has an equivalent diameter of between 1500 and 1850 μm, preferably between 1650 and 1750 μm.

As a variant, the non-traumatic character of the free end may be conferred by the line of the short centring branch 12, which then has a change of direction point and a portion starting from the free end that is substantially colinear with the longitudinal axis of the filter.

The filter may also comprise at least three long centring branches 13, preferably at least 4, at least 5. The qualification "long" should be compared with the qualification "short" of the short centring branches 12. Preferably, the three long centring branches 13 are longer than the anchoring branches (in FIG. 1, one of the long centring branches appears shorter because of the perspective). Preferably 20% to 35%, still preferably 25% to 30%, again preferably approximately 27%, longer than the longest anchoring branch 11. The long centring branches 13 may have different or equal lengths. Preferably they have equal lengths in particular when they terminate in hooks oriented towards the inside of the filter.

Each of the long centring branches 13 has a fixed end and a free end, the fixed end being fixed to the fixed ends of the anchoring branches 11, in particular via the member 15.

The line followed by each long centring branch 13 may have one of the shapes described above. Preferably, the lines followed by the long centring branches 13 have an inflexion point with a convex part between the fixed end and the inflexion point and a concave part between the inflexion point and the free end.

Advantageously, the free end of at least one of the long centring branches 13 comprises a stop 131. The stop 131 makes it possible to push the filter 1, in particular femorally, when it is placed inside the blood vessel. Alternatively, the filter 1 also comprises a contact branch 14 having a fixed end and a free end, the fixed end being fixed to the fixed ends of the anchoring branches 11, in particular via the member 15, and the free end comprising a stop. In both cases, the stop 131 may for example be a loop produced by the corresponding branch. Preferably, the loop forming a stop has an equivalent diameter of between 1700 μm and 2200 μm.

The combination of the long and short centring branches 13, 12 makes it possible to centre the filter with respect to the wall of the blood vessel while limiting or even preventing the tilting of the axis thereof with respect to the local axis of the blood vessel where the filter 1 is placed.

All the branches 11, 12, 13 of the filter advantageously have a cross section with an equivalent diameter of between 0.250 and 0.350 mm, preferably between 0.29 and 0.31 mm, still preferably between 0.295 and 0.305 mm. In the present disclosure, the term "equivalent diameter" of the cross section of a branch designates the diameter of the smallest circle in which the cross section of the branch can be inscribed. Preferably, every branch of the filter has a cross section with the same equivalent diameter over the entire length thereof. Still preferably, all the branches of the filter have a cross section with the same equivalent diameter. Advantageously, the cross section of the branch is a disc.

Preferably, the entire filter 1 is made of stainless steel, preferably INOX 316 LVM.

Preferably the filter 1 has a longitudinal length of between 4.5 and 6.5 cm, still preferably between 5 and 6 cm, for example approximately 5.5 cm. The span of the branches of the filter, that is to say the diameter of the smallest circle the centre of which is aligned on the longitudinal axis of the filter and encompassing all the projections of the branches onto a plane perpendicular to the longitudinal axis of the filter and colinear therewith, is preferably between 4 and 6 cm, still preferably between 4.5 and 5.5 cm, for example approximately 5 cm The description given above corresponds to the filter when it is not constrained by another element external thereto.

Figure 6:
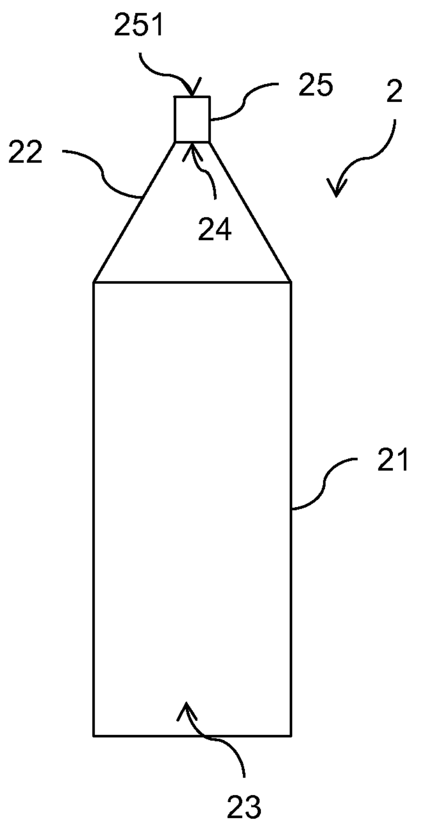
FIG. 6 is an illustration of an adapter for inserting the filter of FIG. 1 inside a catheter.

When it is inserted inside the blood vessel, the branches 11, 12, 13 of the filter are first of all folded, for example by means of an adapter 2. An example of such an adapter 2 (FIG. 6) comprises a cylindrical part 21 with a hollow circular base extended by a hollow conical part 22 truncated at the vertex thereof, having a larger orifice 23 on the cylindrical part side and a smaller orifice 24 on the truncated cone side. The inside surface of the cylindrical part 21 is continuous with that of the conical part 22. The inside diameter of the cylindrical part 21 is sufficiently large for the filter 1 not to be too constrained, or even not at all. The angle at the vertex of the cone is preferably between 50° and 60°, still preferably between 53° and 58°, for example 56°. The cone is truncated so that the inside diameter at the smallest orifice is between 2 mm and 3 mm, preferably between 2.4 and 2.6 mm. The combination of the cone and of the level of truncation enables the branches of the filter to be folded when the filter is disposed inside the adapter so that the free ends of the filter are oriented towards the vertex of the cone and when the filter is pushed inside the adapter 2 through the smaller orifice 24. The filter can then be inserted inside a catheter. For this purpose, the adapter 2 also comprises a connector 25 at the truncation of the cone for connection of the adapter 2 to a catheter. The connector 25 comprises an orifice 251 the diameter of which is at least equal to that of the smallest orifice 24 of the adapter 2. The orifice 251 of the connector is intended to emerge in the aperture of the catheter, in particular a 7 F catheter.

The invention claimed is:

1. A vena cava filter, comprising:

at least two anchoring branches for anchoring the filter in a wall of a blood vessel, the anchoring branches each including a fixed end and a free end, the fixed ends of the anchoring branches being fixed to each other and the free ends each terminating in a hook oriented outwards;

at least three short centering branches, each comprising a fixed end and a free end, the fixed end being fixed to the fixed ends of the anchoring branches, the fixed end and the free end forming a convex line relative to a longitudinal axis of the filter formed by an average of extension axes of the anchoring branches and the short centering branches, wherein each of the anchoring branches comprises an anti-transfixion protection spaced proximal to their respective hook, wherein the anti-transfixion protection comprises a loop, wherein the loop has an equivalent diameter of between 990 pm and 1210 pm, and wherein the vena cava filter is made entirely of stainless steel.

2. The vena cava filter according to claim 1, wherein at least two of the anchoring branches have different lengths.

3. The vena cava filter according to claim 1, wherein the free end of each of the short centering branches is non-traumatic relative to the wall of the vessel in which the filter is to be disposed.

4. The vena cava filter according to claim 3, wherein the non-traumatic free end has a hook oriented inwards.

5. The vena cava filter according to claim 4, wherein the hooks of the short centering branches have an equivalent diameter of between 1500 and 1850 pm.

6. The vena cava filter according to claim 3, wherein the short centering branches have equal lengths or different lengths.

7. The vena cava filter according to claim 3, wherein the short centering branches are between 35% and 55% shorter than the anchoring branches.

8. The vena cava filter according to claim 1, wherein the short centering branches are shorter than the anchoring branches.

9. The vena cava filter according to claim 1, further comprising at least three long centering branches, each having a fixed end and a free end, the fixed end being fixed to the fixed ends of the anchoring branches.

10. The vena cava filter according to claim 9, wherein the long centering branches are longer than the anchoring branches.

11. The vena cava filter according to claim 10, wherein the free end of one of the long centering branches comprises a stop.

12. The vena cava filter according to claim 10, wherein the long centering branches are between 20% and 35% longer than the anchoring branches.

13. The vena cava filter according to claim 1, further comprising a contact branch having a fixed end and a free end, the fixed end being fixed to the fixed ends of the anchoring branches and the free end comprising a stop.

14. The vena cava filter according to claim 13, wherein the stop is a loop produced from the corresponding branch.

15. The vena cava filter according to claim 14, wherein the loop of the corresponding long centering branch has an equivalent diameter between 1700 μm and 2200 μm.

16. The vena cava filter according to claim 1, wherein the stainless steel is INOX 316 LOM.

17. The vena cava filter according to claim 1, wherein the hooks of the anchoring branches have an equivalent diameter between 400 and 1100 pm.

* * * * *